US010039473B2

(12) United States Patent
Zhao et al.

(10) Patent No.: US 10,039,473 B2
(45) Date of Patent: Aug. 7, 2018

(54) SYSTEMS AND METHODS FOR NAVIGATION BASED ON ORDERED SENSOR RECORDS

(71) Applicant: Intuitive Surgical Operations, Inc., Sunnyvale, CA (US)

(72) Inventors: Tao Zhao, Sunnyvale, CA (US); Prashant Chopra, Sunnyvale, CA (US); Vincent Duindam, Mountain View, CA (US); Dorin Panescu, San Jose, CA (US); Lei Fan, Seattle, WA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 319 days.

(21) Appl. No.: 13/892,974

(22) Filed: May 13, 2013

(65) Prior Publication Data

US 2013/0303892 A1 Nov. 14, 2013

Related U.S. Application Data

(60) Provisional application No. 61/759,215, filed on Jan. 31, 2013, provisional application No. 61/646,654, filed on May 14, 2012.

(51) Int. Cl.
*A61B 5/06* (2006.01)
*A61B 5/00* (2006.01)
*A61B 34/20* (2016.01)

(52) U.S. Cl.
CPC .............. *A61B 5/061* (2013.01); *A61B 5/065* (2013.01); *A61B 5/7425* (2013.01); *A61B 34/20* (2016.02); *A61B 2034/2051* (2016.02)

(58) Field of Classification Search
CPC ..................................................... A61B 5/061
See application file for complete search history.

(56) References Cited

U.S. PATENT DOCUMENTS

| | | | |
|---|---|---|---|
| 5,920,319 | A | 7/1999 | Vining et al. |
| 6,380,732 | B1 | 4/2002 | Gilboa |
| 6,389,187 | B1 | 5/2002 | Greenaway et al. |
| 7,901,348 | B2 | 3/2011 | Soper et al. |
| 7,930,065 | B2 | 4/2011 | Larkin et al. |

(Continued)

FOREIGN PATENT DOCUMENTS

| | | |
|---|---|---|
| CN | 1658789 A | 8/2005 |
| CN | 102428496 A | 4/2012 |

(Continued)

OTHER PUBLICATIONS

International Search Report and Written Opinion for Application No. PCT/US2013/040775, dated Aug. 12, 2013, 12 pages.

(Continued)

*Primary Examiner* — Rochelle Turchen

(57) ABSTRACT

A method of tracking a medical instrument comprises receiving a model of an anatomical passageway formation and receiving a set of ordered sensor records for the medical instrument. The set of ordered sensor records provide a path history of the medical instrument. The method further comprises registering the medical instrument with the model of the anatomical passageway formation based on the path history.

43 Claims, 8 Drawing Sheets

(56) References Cited

U.S. PATENT DOCUMENTS

| | | | |
|---|---|---|---|
| 2003/0015207 A1* | 1/2003 | Herold | G06F 19/3437 600/416 |
| 2004/0249267 A1 | 12/2004 | Gilboa | |
| 2006/0013523 A1 | 1/2006 | Childlers et al. | |
| 2006/0062447 A1 | 3/2006 | Rinck et al. | |
| 2006/0069317 A1* | 3/2006 | Horn | A61B 5/065 600/300 |
| 2006/0149134 A1 | 7/2006 | Soper et al. | |
| 2007/0001879 A1 | 1/2007 | Kaftan et al. | |
| 2007/0142749 A1 | 6/2007 | Khatib et al. | |
| 2007/0274579 A1 | 11/2007 | Cai et al. | |
| 2009/0209817 A1 | 8/2009 | Averbuch | |
| 2009/0268955 A1 | 10/2009 | Koolwal et al. | |
| 2011/0224542 A1 | 9/2011 | Mittal et al. | |
| 2012/0029339 A1* | 2/2012 | Cohen | A61B 6/12 600/407 |
| 2012/0069167 A1 | 3/2012 | Liu et al. | |
| 2012/0289777 A1 | 11/2012 | Chopra et al. | |
| 2012/0289843 A1 | 11/2012 | Chopra et al. | |
| 2013/0094745 A1* | 4/2013 | Sundar | G06T 3/0068 382/132 |
| 2013/0303890 A1 | 11/2013 | Duindam et al. | |
| 2013/0303891 A1 | 11/2013 | Chopra | |
| 2013/0303893 A1 | 11/2013 | Duindam et al. | |
| 2013/0303894 A1 | 11/2013 | Duindam et al. | |
| 2014/0235999 A1* | 8/2014 | Birkenbach | A61B 19/5244 600/424 |

FOREIGN PATENT DOCUMENTS

| | | |
|---|---|---|
| JP | 2007531543 A | 11/2007 |
| WO | WO-2005008591 A2 | 1/2005 |
| WO | WO-2006070669 A1 | 7/2006 |
| WO | WO-2007129616 A1 | 11/2007 |
| WO | WO-2009064715 A1 | 5/2009 |
| WO | WO-2011102012 A1 | 8/2011 |
| WO | WO-2012035492 A1 | 3/2012 |

OTHER PUBLICATIONS

LAN/MAN Standards Committee, "Part 11: Wireless LAN Medium Access Control (MAC) and Physical Layer (PHY) Specifications," IEEE Standard for Information technology, Telecommunications and Information Exchange Between Systems, Local and Metropolitan Area Networks, Specific Requirements, IEEE Std 802.11-2012 (Revision of IEEE Std 802.11.2007), IEEE Computer Society, Mar. 29, 2012, 2793 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. 13791626.8, dated Jul. 18, 2016, 7 pages.

Co-pending U.S. Appl. No. 60/588,336, filed Jul. 16, 2004.

\* cited by examiner

| | TIME | POSITION | ORIENTATION | SHAPE |
|---|---|---|---|---|
| 322 | T1 | x1 | u1 | h1 |
| 324 | T2 | x2 | u2 | h2 |
| 326 | T3 | x3 | u3 | h3 |
| 328 | T4 | x4 | u4 | h4 |
| 330 | T5 | x5 | u5 | h5 |
| 332 | T6 | x6 | u6 | h6 |

SYSTEMS AND METHODS FOR NAVIGATION BASED ON ORDERED SENSOR RECORDS

CROSS-REFERENCE TO RELATED APPLICATIONS

This application claims the benefit of U.S. Provisional Application 61/646,654 filed May 14, 2012, and of U.S. Provisional Application 61/759,215 filed Jan. 31, 2013, which are incorporated by reference herein in their entirety.

FIELD

The present disclosure is directed to systems and methods for navigating a patient anatomy to conduct a minimally invasive procedure, and more particularly to systems and methods for tracking an instrument by registering temporally ordered sensor information with a model of the patient anatomy.

BACKGROUND

Minimally invasive medical techniques are intended to reduce the amount of tissue that is damaged during interventional procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert interventional instruments (including surgical, diagnostic, therapeutic, or biopsy instruments) to reach a target tissue location. To reach the target tissue location, a minimally invasive interventional instrument may navigate natural or surgically created passageways in anatomical systems such as the lungs, the colon, the intestines, the kidneys, the heart, the circulatory system, or the like. To assist the clinician in navigating the instrument through the passageways, models of the passageway are prepared using pre-operative or inter-operative imaging. Current systems for tracking the movement of the instrument relative to the modeled passageways are vulnerable to error because precisely locating a portion of the instrument, such as the tip, in a dense thicket of narrow anatomical passageways is often challenging. Improved systems and methods are needed for registering a portion of the instrument to the model of the anatomic passageways to track movement of the instrument relative to the model of the anatomy.

SUMMARY

The embodiments of the invention are summarized by the claims that follow the description.

In one embodiment, a method of tracking a medical instrument comprises receiving a model of an anatomical passageway formation and receiving a set of ordered sensor records for the medical instrument. The set of ordered sensor records provide a path history of the medical instrument. The method further comprises registering the medical instrument with the model of the anatomical passageway formation based on the path history.

In another embodiment, a system comprises a processor configured for receiving a model of an anatomical passageway formation and receiving a set of ordered sensor records for a medical instrument equipped with a sensor. The set of ordered sensor records provides a path history of the medical instrument. The processor is further configured for registering the medical instrument with the model of the anatomical passageway formation based on the path history.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
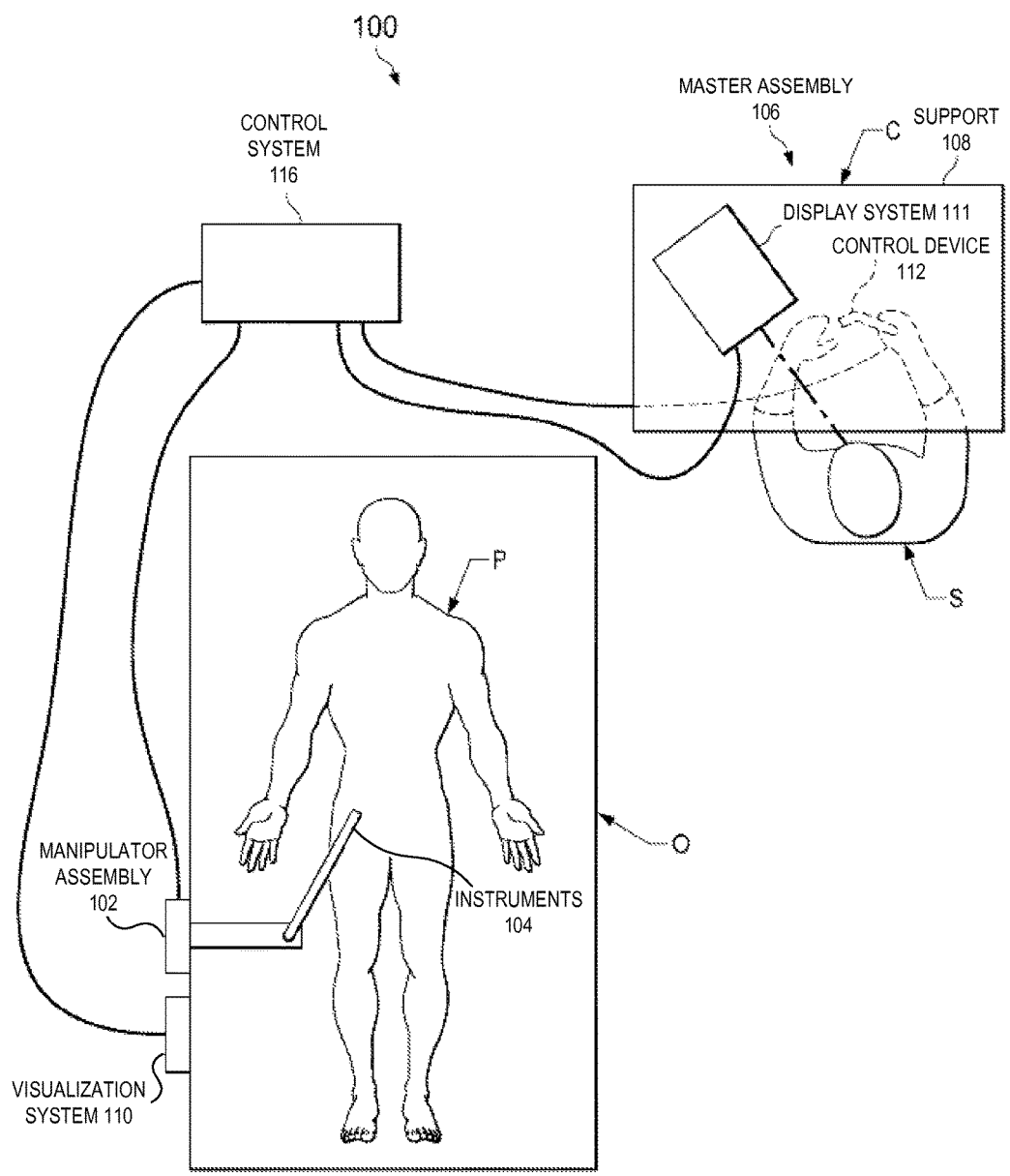
FIG. 1 is a robotic interventional system, in accordance with embodiments of the present disclosure.

Referring to FIG. 1 of the drawings, a robotic interventional system for use in, for example, surgical, diagnostic, therapeutic, or biopsy procedures, is generally indicated by the reference numeral 100. As shown in FIG. 1, the robotic system 100 generally includes an interventional manipulator assembly 102 for operating an interventional instrument 104 in performing various procedures on the patient P. The assembly 102 is mounted to or near an operating table O. A master assembly 106 allows the surgeon S to view the surgical site and to control the slave manipulator assembly 102.

The master assembly 106 may be located at a surgeon's console C which is usually located in the same room as operating table O. However, it should be understood that the surgeon S can be located in a different room or a completely different building from the patient P. Master assembly 106 generally includes an optional support 108 and one or more control device(s) 112 for controlling the manipulator assemblies 102. The control device(s) 112 may include any number of a variety of input devices, such as joysticks, trackballs, data gloves, trigger-guns, hand-operated controllers, voice recognition devices, body motion or presence sensors, or the like. In some embodiments, the control device(s) 112 will be provided with the same degrees of freedom as the associated interventional instruments 104 to provide the surgeon with telepresence, or the perception that the control device(s) 112 are integral with the instruments 104 so that the surgeon has a strong sense of directly controlling instruments 104. In other embodiments, the control device(s) 112 may have more or fewer degrees of freedom than the associated interventional instruments 104 and still provide the surgeon with telepresence. In some embodiments, the control device(s) 112 are manual input devices which move with six degrees of freedom, and which may also include an actuatable handle for actuating instruments (for example, for closing grasping jaws, applying an electrical potential to an electrode, delivering a medicinal treatment, or the like).

In alternative embodiments, the robotic system may include more than one slave manipulator assembly and/or more than one master assembly. The exact number of manipulator assemblies will depend on the surgical procedure and the space constraints within the operating room, among other factors. The master assemblies may be collocated, or they may be positioned in separate locations. Multiple master assemblies allow more than one operator to control one or more slave manipulator assemblies in various combinations.

An optional visualization system 110 may include an endoscope system such that a concurrent (real-time) image of the surgical site is provided to surgeon console C. The concurrent image may be, for example, a two- or three-dimensional image captured by an endoscopic probe positioned within the surgical site. In this embodiment, the visualization system 110 includes endoscopic components that may be integrally or removably coupled to the interventional instrument 104. In alternative embodiments, however, a separate endoscope attached to a separate manipulator assembly may be used to image the surgical site. Alternatively, a separate endoscope assembly may be directly operated by a user, without robotic control. The endoscope assembly may include active steering (e.g., via teleoperated steering wires) or passive steering (e.g., via guide wires or direct user guidance). The visualization system 110 may be implemented as hardware, firmware, software, or a combination thereof, which interacts with or is otherwise executed by one or more computer processors, which may include the processor(s) of a control system 116.

A display system 111 may display an image of the surgical site and interventional instruments captured by the visualization system 110. The display 111 and the master control device(s) 112 may be oriented such that the relative positions of the imaging device in the scope assembly and the interventional instruments are similar to the relative positions of the surgeon's eyes and hand(s) so the operator can manipulate the interventional instrument 104 and the master control device(s) 112 as if viewing the workspace in substantially true presence. True presence means that the displayed tissue image appears to an operator as if the operator was physically present at the imager location and directly viewing the tissue from the imager's perspective.

Alternatively or additionally, display system 111 may present images of the surgical site recorded and/or modeled preoperatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. The presented preoperative images may include two-dimensional, three-dimensional, or four-dimensional (including e.g., time based or velocity based information) images.

In some embodiments, the display system 111 may display a virtual visualization image in which the actual location of the interventional instrument is registered (e.g., dynamically referenced) with preoperative or concurrent images to present the surgeon S with a virtual image of the internal surgical site at the location of the tip of the surgical instrument.

In other embodiments, the display system 111 may display a virtual visualization image in which the actual location of the interventional instrument is registered with prior images (including preoperatively recorded images) or concurrent images to present the surgeon S with a virtual image of an interventional instrument at the surgical site. An image of a portion of the interventional instrument may be superimposed on the virtual image to assist the surgeon controlling the interventional instrument.

As shown in FIG. 1, a control system 116 includes at least one processor (not shown), and typically a plurality of processors, for effecting control between the slave surgical manipulator assembly 102, the master assembly 106, the visualization system 110, and the display system 111. The control system 116 also includes programmed instructions (e.g., a computer-readable medium storing the instructions) to implement some or all of the methods described herein. While control system 116 is shown as a single block in the simplified schematic of FIG. 1, the system may comprise a number of data processing circuits (e.g., on the slave surgical manipulator assembly 102 and/or on the master assembly 106), with at least a portion of the processing optionally being performed adjacent the slave surgical manipulator assembly, a portion being performed the master assembly, and the like. Any of a wide variety of centralized or distributed data processing architectures may be employed. Similarly, the programmed instructions may be implemented as a number of separate programs or subroutines, or they may be integrated into a number of other aspects of the robotic systems described herein. In one embodiment, control system 116 supports wireless communication protocols such as Bluetooth, IrDA, HomeRF, IEEE 802.11, DECT, and Wireless Telemetry.

In some embodiments, control system 116 may include one or more servo controllers to provide force and torque feedback from the interventional instruments 104 to one or more corresponding servomotors for the control device(s) 112. The servo controller(s) may also transmit signals instructing manipulator assembly 102 to move instruments which extend into an internal surgical site within the patient body via openings in the body. Any suitable conventional or specialized servo controller may be used. A servo controller may be separate from, or integrated with, manipulator assembly 102. In some embodiments, the servo controller and manipulator assembly are provided as part of a robotic arm cart positioned adjacent to the patient's body.

Each manipulator assembly 102 supports a interventional instrument 104 and may comprise a kinematic structure of one or more non-servo controlled links (e.g., one or more links that may be manually positioned and locked in place, generally referred to as a set-up structure) and a robotic manipulator. The robotic manipulator assembly 102 is driven by a plurality of actuators (e.g., motors). These motors actively move the robotic manipulators in response to commands from the control system 116. The motors are further coupled to the interventional instrument so as to advance the interventional instrument into a naturally or surgically created anatomical orifice and to move the distal end of the interventional instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors can be used to actuate an articulable end effector of the instrument for grasping tissue in the jaws of a biopsy device or the like.

Figure 2:
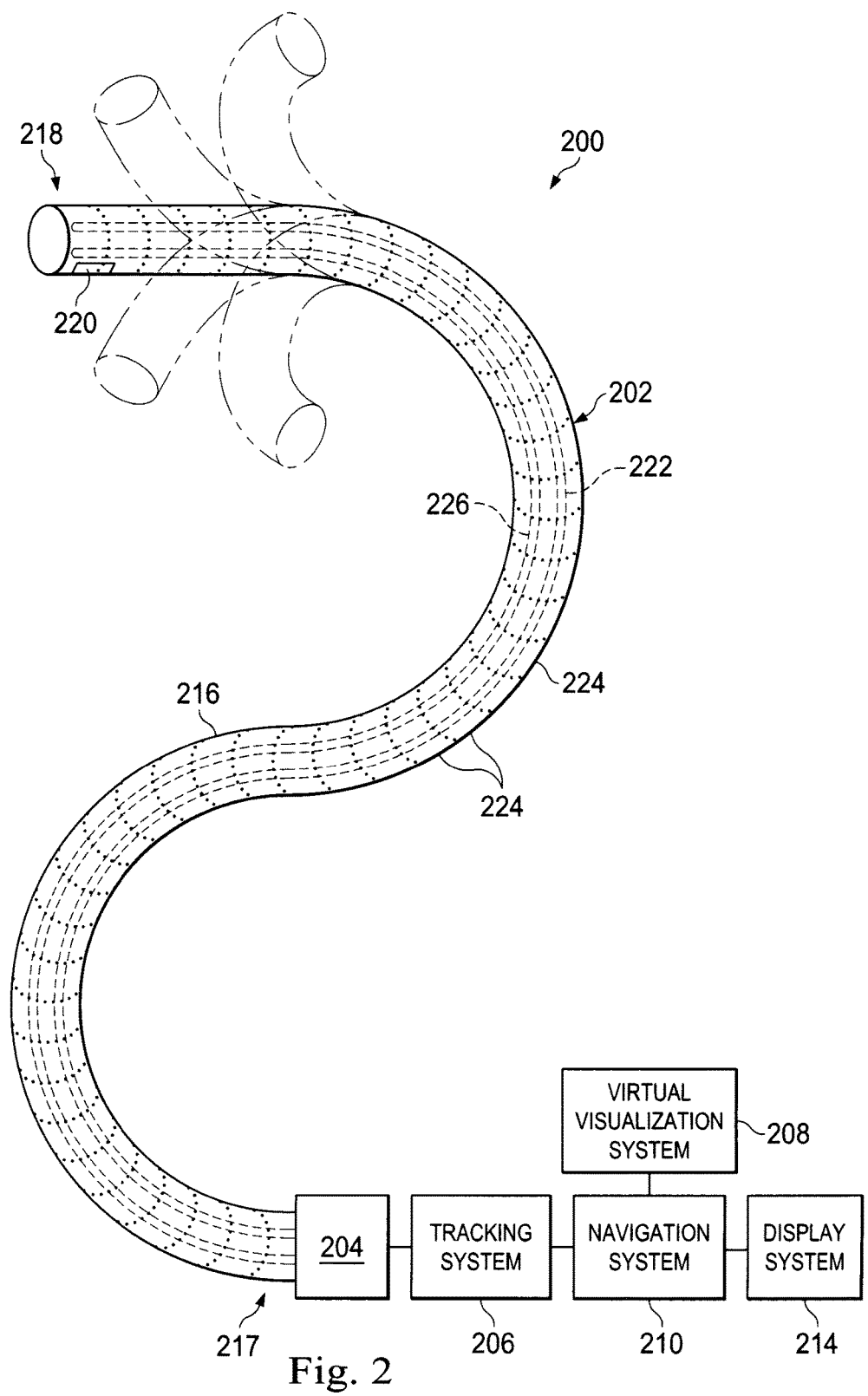
FIG. 2 illustrates an interventional instrument system utilizing aspects of the present disclosure.

FIG. 2 illustrates a minimally invasive system 200 utilizing aspects of the present disclosure. The system 200 may be incorporated into a robotic interventional system, such as system 100. Alternatively, the system 200 may be used for non-robotic exploratory procedures or in procedures involving traditional manually operated interventional instruments, such as endoscopy. The system 200 includes a catheter system 202 (e.g., part of the instrument 104) coupled by an interface unit 204 to a tracking system 206. A navigation system 210 (e.g., part of the control system 116) processes information from a virtual visualization system 208 and the tracking system 206 to generate a virtual image display on a display system 214 (e.g., part of the display system 111). The system 200 may further include optional operation and support systems (not shown) such as imaging systems, illumination systems, steering control systems, irrigation systems, and/or suction systems.

The catheter system 202 includes an elongated flexible body 216 having a proximal end 217 and a distal end 218. In one embodiment, the flexible body 216 has an approximately 3 mm outer diameter. Other flexible body outer diameters may be larger or smaller. The catheter system 202 includes a sensor system which includes a position sensor system 220 (e.g., an electromagnetic (EM) sensor system) and/or a shape sensor system 222 for determining the position, orientation, speed, pose, and/or shape of the catheter tip at distal end 218 and/or of one or more segments 224 along the body 216. The entire length of the body 216, between the distal end 218 and the proximal end 217 may be effectively divided into the segments 224. The position sensor system 220 and the shape sensor system 222 interface with the tracking system 206. The tracking system 206 may be implemented as hardware, firmware, software or a combination thereof which interact with or are otherwise executed by one or more computer processors, which may include the processors of a control system 116.

The position sensor system 220 may be an EM sensor system that includes one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

The shape sensor system 222 includes an optical fiber aligned with the flexible body 216 (e.g., provided within an interior channel (not shown) or mounted externally). The tracking system 206 may be coupled to a proximal end of the optical fiber. In one embodiment, the optical fiber has a diameter of approximately 200 μm. In other embodiments, the dimensions may be larger or smaller.

The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389, filed Jul. 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and Fluorescence scattering may be suitable. In other alternative embodiments, the shape of the catheter may be determined using other techniques. For example, if the history of the catheter's distal tip pose is stored for an interval of time that is smaller than the period for refreshing the navigation display or for alternating motion (e.g., inhalation and exhalation), the pose history can be used to reconstruct the shape of the device over the interval of time. As another example, historical pose, position, or orientation data may be stored for a known point of an instrument along a cycle of alternating motion, such as breathing. This stored data may be used to develop shape information about the catheter. Alternatively, a series of positional sensors, such as EM sensors, positioned along the catheter can be used for shape sensing. Alternatively, a history of data from a positional sensor, such as an EM sensor, on the instrument during a procedure may be used to represent the shape of the instrument, particularly if an anatomical passageway is generally static. Alternatively, a wireless device with position or orientation controlled by an external magnetic field may be used for shape sensing. The history of its position may be used to determine a shape for the navigated passageways.

In this embodiment, the optical fiber may include multiple cores within a single cladding. Each core may be single-mode with sufficient distance and cladding separating the cores such that the light in each core does not interact significantly with the light carried in other cores. In other embodiments, the number of cores may vary or each core may be contained in a separate optical fiber.

In some embodiments, an array of FBG's is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBG's, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBG's produce a reflected wavelength that is a function of the strain on the fiber and its temperature. This FBG technology is commercially available from a variety of sources, such as Smart Fibres Ltd. of Bracknell, England. Use of FBG technology in position sensors for robotic surgery is described in U.S. Pat. No. 7,930,065, filed Jul. 20, 2006, disclosing "Robotic Surgery System Including Position Sensors Using Fiber Bragg Gratings," which is incorporated by reference herein in its entirety.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. For example, regions of the cores containing FBG's, if located at points where the fiber is bent, can thereby be used to determine the amount of bending at those points. These data, combined with the known spacings of the FBG regions, can be used to reconstruct the shape of the fiber. Such a system has been described by Luna Innovations. Inc. of Blacksburg, Va.

As described, the optical fiber may be used to monitor the shape of at least a portion of the catheter system 202. More specifically, light passing through the optical fiber is processed by the tracking system 206 for detecting the shape of the catheter system 202 and for utilizing that information to assist in surgical procedures. The tracking system 206 may include a detection system for generating and detecting the light used for determining the shape of the catheter system 202. This information, in turn, in can be used to determine other related variables, such as velocity and acceleration of the parts of an interventional instrument. The sensing may be limited only to the degrees of freedom that are actuated by the robotic system, or may be applied to both passive (e.g., unactuated bending of the rigid members between joints) and active (e.g., actuated movement of the instrument) degrees of freedom.

The flexible body 216 may optionally house an image capture probe 226. The image capture probe 226 includes a tip portion with a stereoscopic or monoscopic camera disposed near the distal end 218 of the flexible body 216 for capturing images (including video images) that are transmitted to and processed by the navigation system 210 for display. The image capture probe 226 may include a cable coupled to the camera for transmitting the captured image data. Alternatively, the image capture instrument may be a fiber-optic bundle, such as a fiberscope, that couples to the imaging system. The image capture instrument may be single or multi-spectral, for example capturing image data in the visible spectrum, or capturing image data in the visible and infrared or ultraviolet spectrums.

The body 216 may also house cables, linkages, or other steering controls (not shown) that extend between the interface 204 and the tip distal end 218 to controllably bend or turn the distal end 218 as shown for example by the dotted line versions of the distal end. The catheter system may be steerable or, alternatively, may be non-steerable with no integrated mechanism for operator control of the instrument bending. The flexible body 216 may further house control mechanisms (not shown) for operating a surgical end effector or another working distal part that is manipulable for a medical function, e.g., for effecting a predetermined treatment of a target tissue. For instance, some end effectors have a single working member such as a scalpel, a blade, an optical fiber, or an electrode. Other end effectors may include pair or plurality of working members such as forceps, graspers, scissors, or clip appliers, for example. Examples of electrically activated end effectors include electrosurgical electrodes, transducers, sensors, and the like. Also or alternatively, the flexible body 216 can define one or more lumens through which interventional instruments can be deployed and used at a target surgical location.

The virtual visualization system 208 provides navigation assistance to the catheter system 202. Virtual navigation using the virtual visualization system is based upon reference to an acquired dataset associated with the three dimensional structure of the anatomical passageways. More specifically, the virtual visualization system 208 processes images of the surgical site recorded and/or modeled using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software is used to convert the recorded images into a two dimensional or three dimensional model of a partial or an entire anatomical organ or anatomical region. The model describes the various locations and shapes of the passageways and their connectivity. The images used to generate the model may be recorded preoperatively or intra-operatively during a clinical procedure. In an alternative embodiment, a virtual visualization system may use standard models (i.e., not patient specific) or hybrids of a standard model and patient specific data. The model and any virtual images generated by the model may represent the static posture of a deformable anatomic region during one or more phases of motion (e.g., during an inspiration/expiration cycle of a lung).

During a virtual navigation procedure, the sensor systems may be used to compute an approximate location of the instrument with respect to the patient anatomy. The location can be used to produce both macro-level tracking images of the patient anatomy and virtual internal images of the patient anatomy. Various systems for using fiber optic sensors to register and display an interventional implement together with preoperatively recorded surgical images, such as those from a virtual visualization system, are known. For example U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety, discloses one such system.

Existing systems and methods for locating the tip of the catheter and accurately registering it with an anatomic passageway model from the virtual visualization system are often not entirely adequate, particularly in portions of the anatomy, such as the lungs, where airway passages are narrow and densely arranged. These prior approaches are subject to inaccuracies due to measurement precision limits and anatomic movement (e.g., patient breathing or tissue deformation in response to surgical instrumentation). For example, the positional information provided by an EM sensor may be accurate to approximately +/−3 mm with respect to a lung after registration to patient anatomy model, using reference fiducials on the chest. When motion of the lungs is considered, the error may increase up to approximately +/−10 mm or more. These errors may cause the instrument tip to become registered to the wrong passageway of the anatomic model or may result in the sensor system generating a location for the tip of the catheter that is outside of an anatomic passageway. As the catheter moves through the passageway system, these errors can cause the instrument to unrealistically jump between modeled passageways as the catheter tip is advanced. If the location of the tip of the catheter is incorrectly determined, the virtual visualization system will return an incorrect virtual view from the distal end of the catheter (e.g., showing the probe in the wrong branch of the airway tree) therefore giving inaccurate guidance to the clinician.

In embodiments of the present disclosure, temporal or spatial ordering of the sensor data is utilized in a probabilistically reasoning framework to improve the limitations mentioned above. Temporally ordered historical data (i.e, chronologically sequenced data records) from the sensor system may be processed by the navigation system 210 to register and track the catheter tip with respect to an anatomic passageway model from the virtual visualization system 208. The temporally ordered historical data may be generated, for example, from an EM sensor located on the catheter. Alternatively or additionally, spatially ordered data (i.e., data records arranged in order along the shape of catheter and optionally recorded at fixed intervals) from the sensor system may be processed by the navigation system to register and track the catheter with respect to an anatomic passageway model. The spatially ordered data may be generated, for example, from a fiber shape sensor extending within the catheter. A temporally ordered data set, a spatially ordered data set, or a single set of shape data can provide a path history of the catheter. Other information, such as airway topology and physical constraints, may also be used with the ordered sensor data to provide a probabilistic method for tracking the catheter tip through the anatomic passageways. The use of this additional information may be used with current sensor information to more accurately locate the catheter tip relative to the model and generate a virtual image of the anatomy that corresponds to the true location of the catheter tip. The clinician navigating the instrument is, thus, less likely to guide the catheter to unintended locations, minimizing the need for time-consuming and potentially injurious backtracking.

Figures 3A, 3B:
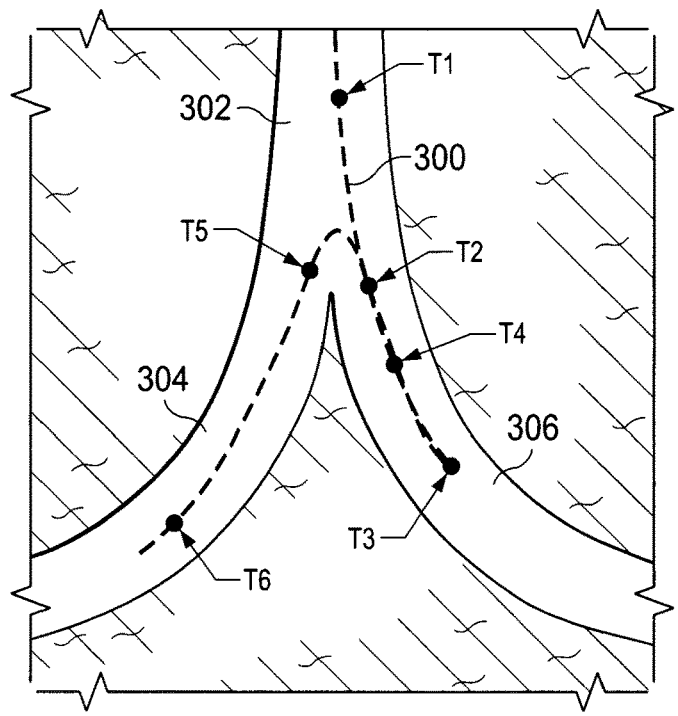
FIG. 3a illustrates a path of an interventional instrument within a patient anatomy.
FIG. 3b illustrates a table of temporally ordered sensor records.

FIG. 3a illustrates a path 300 of the tip of an interventional instrument (such as catheter system 202) within branches 302, 304, 306 of a patient anatomy. As the instrument is advanced within the patient anatomy, sensor records are generated at time instances T1-T6. At T1, the tip is within the branch 302. At T2, the tip has entered the branch 306. At T3, the tip is within the branch 306. At T4, the tip has reversed directions and is being withdrawn from the branch 306. At T5, the tip has entered the branch 304. At T6, the tip is within the branch 304.

FIG. 3b illustrates a table 320 of temporally ordered sensor records 322-332 associated with time instances T1-T6, respectively, along the trajectory of path 300. In this embodiment, for example, the sensor record 322 is gathered at time T1 and catalogs the position x1, the unit orientation vector u1, and shape data h1 of a portion of the instrument such as the tip. The position and unit orientation vector may be based upon a position sensor, such as an sensor, and the shape data may be based upon a shape sensor. The position data may include, for example, three degrees of freedom information (e.g., X, Y, Z coordinates in a Cartesian system). The unit orientation information may include three degrees of freedom information (e.g., pitch, yaw, roll).

The common table format of FIG. 3b, is for illustration only and poses no limitations on how the data associated with each time instance is stored. For example, each type of data (e.g., position, orientation, shape) may be maintained in separate databases. Alternatively, data associated with different sensor systems (e.g., position sensor system, shape sensor system) may be maintained separately and for different time instances. Also, no limitation is imposed on the type of data that may be stored for each time instance. Sensor records may be stored as individual files or may be stored in one or more databases. Alternatively, some other data management system may be used. The present disclosure imposes no limitations on how the sensor records are stored or what information is associated with a sensor record.

Figure 4:
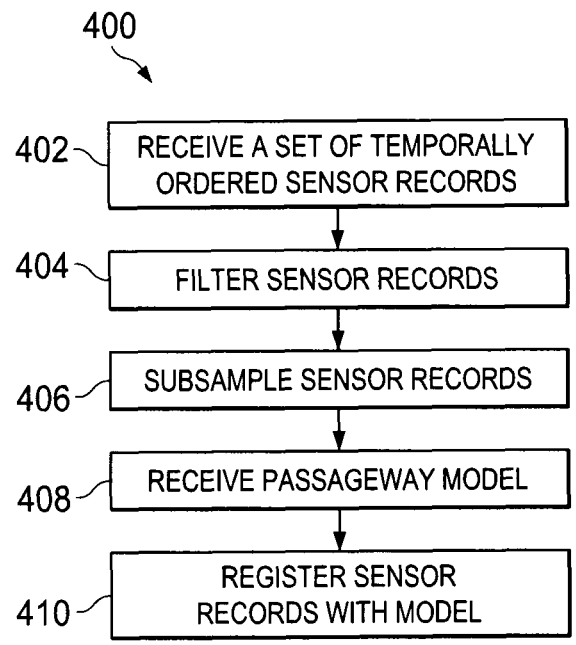
FIG. 4 is a flowchart describing a method of tracking an interventional instrument.

FIG. 4 is a flowchart describing a method of tracking an interventional instrument (such as catheter system 202) with respect to a model of a patient anatomy. At 402, a full or partial set of sensor records are received in a temporal order at a processor (e.g. the processors of control system 116). Alternatively, the sensor records may include time sequencing information that allows the records to be arranged in a temporal order after receipt.

At 404, the sensor records are, optionally, filtered to remove sensor records from the set or to remove information from selected sensor records in the set. For example, the sensor record set may be edited to include only those sensor records along a direct path from a root record (e.g., T1) to a current record (e.g., T6). In this example, the sensor records for T2, T3, and T4 would be dropped, with the sensor record for T1, T5, and T6 remaining in the set to be analyzed. Additionally or alternatively, the sensor record set may be edited to include only data associated with a selected phase of cyclical patient movement (e.g., breathing motion). For example, a gating signal associated with a phase of respiration, such as expiration, may be provided that allows only sensor records associated with the lung in a state of expiration to be included in a subset of data for analysis. Gating is used to minimize the deviation of the sensor data from the model and eliminate outlying data records, providing a more coherent data set associated with the effective trajectory of the interventional instrument. Further description of systems and methods for gathering and analyzing data associated with cyclical patient movements is provided in U.S. patent application Ser. No. 13/297,066, filed Nov. 15, 2011, disclosing "Method and System for Determining Information of Extrema During Expansion and Contraction Cycles of an Object," which is incorporated by reference herein in its entirety. The filtered subset of sensor records may be used to determine a velocity for the instrument tip between time instances. The calculated velocity vector may or may not be the same as the pointing direction associated with the sensor record. In some cases, the velocity vector may match the path direction better than the pointing direction associated with the sensor record. Estimating velocity from incoming positional data (e.g., using a Kalman filter) has inherent latency. Additionally or alternatively velocity estimation can be computed by positional data both before and after the time instant being estimated (e.g., using Kalman smoothing).

To limit the influence of long pauses in motion or very slow velocities, at 406, the sensor records may be further subsampled at a selected spatial resolution. For example, a spatial resolution of one sample per millimeter may be selected for subsampling the sensor records. The spatial resolution may be selected to correspond the spatial resolution of the imaging technology used to generate the model (e.g., the CT spatial resolution). Spatial subsampling would eliminate a repeat sensor record from the subset if the tip of the instrument is stopped for an extended period of time. Trajectory orientation estimation may, optionally, be performed after spatial subsampling to avoid an undefined velocity when the device does not move or moves very slowly. After subsampling at 406, the resultant subset of sensor records may have an equal spatial spacing.

At 408, the model of the anatomic passageways is received from the virtual visualization system. At 410, the trajectory of the tip of the catheter is registered with the model of the anatomic passageways. Generally, for each passageway in the model, a centerline or any other sampled line through the modeled passageway is determined from the model. The sensor trajectory is registered with the model by matching the subset of sensor records to the sampled line through the modeled passageway.

Figure 5:
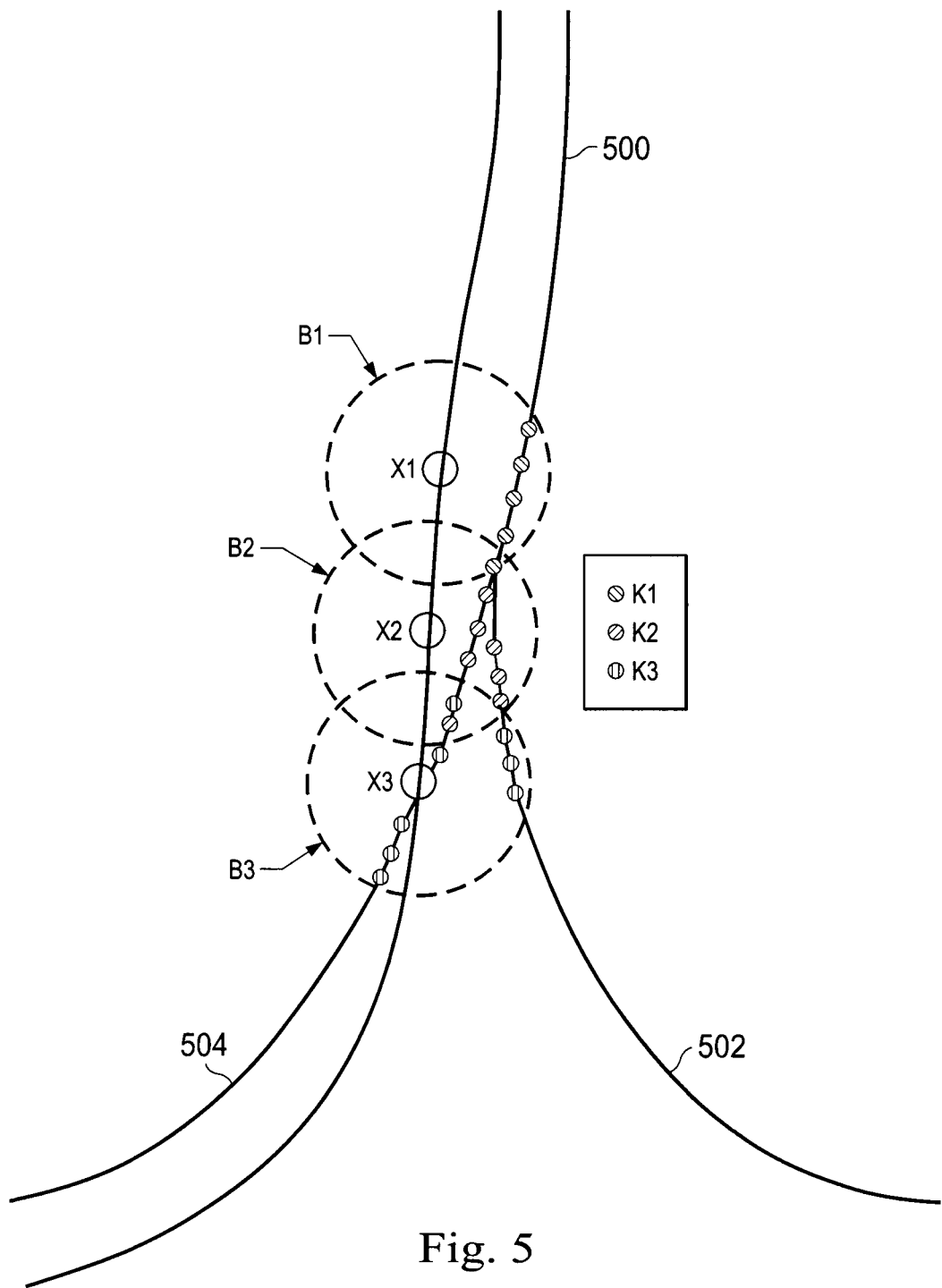
FIG. 5 illustrates temporally ordered sensor data and candidate match points along a model of anatomic passageways.

In one illustrative example, the subset of sensor records are temporally ordered and spatially sampled EM sensor records generated by an EM sensor located near the tip of an interventional instrument. In this embodiment, centerlines through the modeled anatomic passageways are comprised of a series of centerline points labeled $L_i$, where $i=1, \ldots, M$ and M is the total number of centerline points. Each centerline point $L_i$ has a three-dimensional coordinate, $P_i$, and a unit orientation vector $O_i$. FIG. 5 illustrates centerlines 500, 502, 504 formed of centerline points $L_i$. Each EM sensor record includes an observation labeled $X_i=[x_i, u_i]$ where $x_i$ is the three-dimensional coordinate for the observation and $u_i$ is the unit orientation vector for the observation. To determine the centerline point $L_i$ that is best matched to each EM observation, a solution $S=[s_1, \ldots, s_n]$ is calculated. The solution is expressed as $S^*=\mathrm{argmax}(P(XX|S))$, where $$P(XX \mid S) = \prod_{i=1}^{n} P(X_i \mid s_i) \prod_{i=2}^{n} P(s_i \mid s_{i1}) P(s_1).$$

Figure 6:
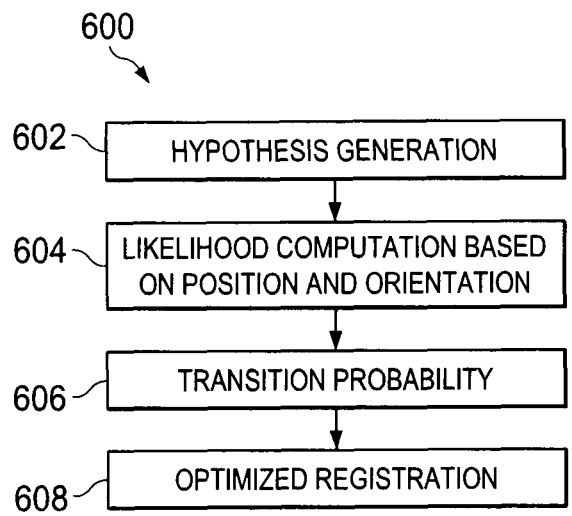
FIG. 6 is a flowchart describing the registration of a sensor trajectory to an anatomic model.

As shown in FIG. 6, a process 600 for registering the sensor trajectory with the model includes at 602, generating a hypothesis by identifying candidate centerline points that correspond to, for example the temporally ordered EM sensor records. At 604, a candidate point likelihood computation is performed based upon candidate point position and orientation. At 606, a transition probability between candidate points is calculated. At 608, the state likelihood computations and transition probability computations are used to optimize the model registration.

In one embodiment, we constrain the candidates to be on the centerline of the passage. One can also use other methods to generate discrete candidates. In greater detail, the initial step of hypothesis generation includes best matching each sensor observation $X_i$ to a centerline point $L_i$. As shown in FIG. 5, for each $X_i$ ($X_1, X_2, X_3, \ldots$), there is a finite set of candidate centerline points $K_i$ ($K_1, K_2, K_3, \ldots$) (i.e., subset of the centerline points $L_i$) within each sensor error boundary $B_i$ ($B_1, B_2, B_3, \ldots$). The candidate points $K_i$ for each boundary set may overlap. Each centerline point $K_i$ is a hypothetical possible match for the sensor observation $X_i$. Although FIG. 5 describes multiple hypotheses for each observation $X_i$, in other various embodiments, a single best match centerline point K for each piece of the passage may be chosen within each error boundary B.

Next, a likelihood computation is performed by matching position and orientation information for each EM sensor observation $X_i$ to position and orientation information for a centerline point $L_i$. Likelihood measures how likely an EM observation is generated by the state (i.e., how likely one of the centerline points in the set $K_i$ is a match for the EM sensor observation $X_i$). The likelihood computation includes the position matching term ($x_i$) and the orientation matching term ($u_i$) for sensor record $X_i$:

$$P(X_i \mid s_i) \propto \exp\left\{-\frac{\|x_i - P_{si}\|^{\wedge}2}{\sigma_1^2}\right\}\exp\left\{-\frac{(\mathrm{arccos}\,dot(u_i,\sigma_{si}))^{\wedge}2}{\sigma_2^2}\right\}.$$

Next, in the process of best matching each temporally ordered EM sensor observation $X_i$ to a centerline point $L_i$ is a transition probability computation. Transition probability measures the likelihood of one state change to the next state. For example, transition probability may measure the likelihood that a sequential pair of candidate centerline points is best matched to a pair of EM sensor observations. Alternatively, the transition probability may be defined without sensor observations. Transition probability computation may apply penalties to unlikely sequential candidate centerline points or otherwise place constraints on sequential pairs. For example, a jump between a candidate centerline points that are far away from each other would be penalized as compared to candidate centerline points that are closer together. Other constraints may also be encoded. For example, a penalty may be placed on state transitions that do not consider sensor inputs.

$$P(s_i \mid s_{i-1}) = \exp\left\{-\frac{\|P_{si} - P_{si-1}\|^2}{2\sigma_3^2}\right\}.$$

As another example, a penalty may be placed on state transitions considering sensor input by matching the vector of sensor input and the vector of the states.

$$P(s_i \mid s_{i-1}) = \exp\left\{-\frac{\|(P_{si} - P_{si-1}) - (x_i - x_{i-1})\|^2}{2\sigma_3^2}\right\}$$

As another example, state transitions may be confined to occur only on the centerline tree structure, where D( ) is the distance along the tree structure.

$$P(s_i \mid s_{i-1}) = \exp\left\{-\frac{(\|x_i - x_{i-1}\| - D(s_i, s_{i-1}))^2}{2\sigma_3^2}\right\}$$

This enforces the topological constraint on the matching methodology. The direction of the motion may also be used to further refine the matching.

When the sensor observation is associated with a significant amount of noise, the distance $\|x_i - x_{i-1}\|$ is always greater than the actual $D(s_i, s_{i-1})$. This may lead to a tendency to choose sequential candidate centerline points with a larger than actual distance in order to match the noisy sensor input. To minimize the effect of this noise, the sensor motion vector may be projected to the centerline direction. For example, in the following expression, the second term penalizes a high angle difference between the sensor motion vector and the state motion vector (i.e., the candidate centerline point motion vector).

$$P(s_i \mid s_{i-1}) = \\ \exp\left\{-\frac{(\|x_i - x_{i-1}\| - D(s_i, s_{i-1}))^2}{2\sigma_3^2}\right\}\exp\left\{-\frac{\left\|(x_i - \tilde{x}_{i-1}) - (P_{si} - \tilde{P}_{si-1})\right\|^{\wedge}2}{2\sigma_4^2}\right\}$$

The direction of the path within the centerline tree structure may also be used to augment the matching process. For example, if the directions associated with the candidate centerline points change but the actual motor or manual manipulation of the instrument never changed direction, then the pair of candidate centerline points should be considered impossible. The aforementioned pair-wise constraints may enforce some transition smoothing, but additional optimization may further refine the matching.

Transition probability may also consider the consistency of error. The sensor observation records are not truly independent due to the smooth nature of deformation. Gross deformation may be compensated in the probability calculation by using term below in the transition probability. It is in favor of slow changing of the error vectors (vector from state to sensor input)

$$\exp\left\{-\frac{\|(x_i - P_{si}) - (x_{i-1} - P_{si-1})\|^2}{2\sigma_5^2}\right\}.$$

Global optimization may be solved, for example, by entering the computed likelihoods and transition probabilities into a table and using dynamic programming (e.g., the Viterbi algorithm) to compute a solution. For each time instant T, the best trajectory estimate is based upon the prior temporally ordered sensor records.

Figure 8:
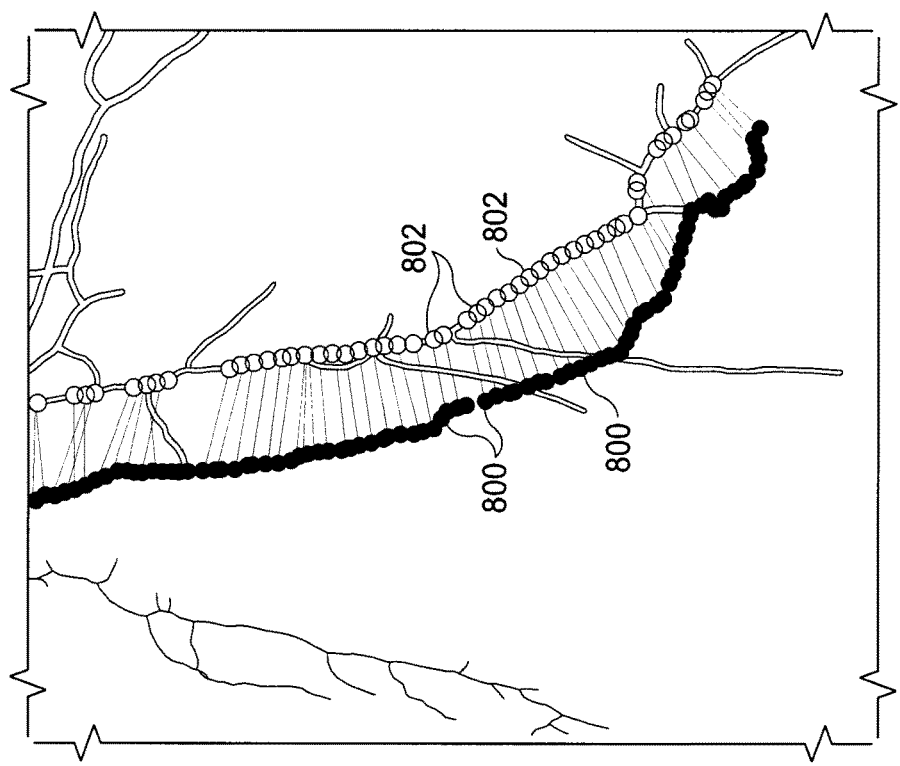
FIGS. 7-8 illustrate temporally ordered sensor data and candidate match points along a model of anatomic passageways according to embodiments of the present disclosure.
Figure 7:
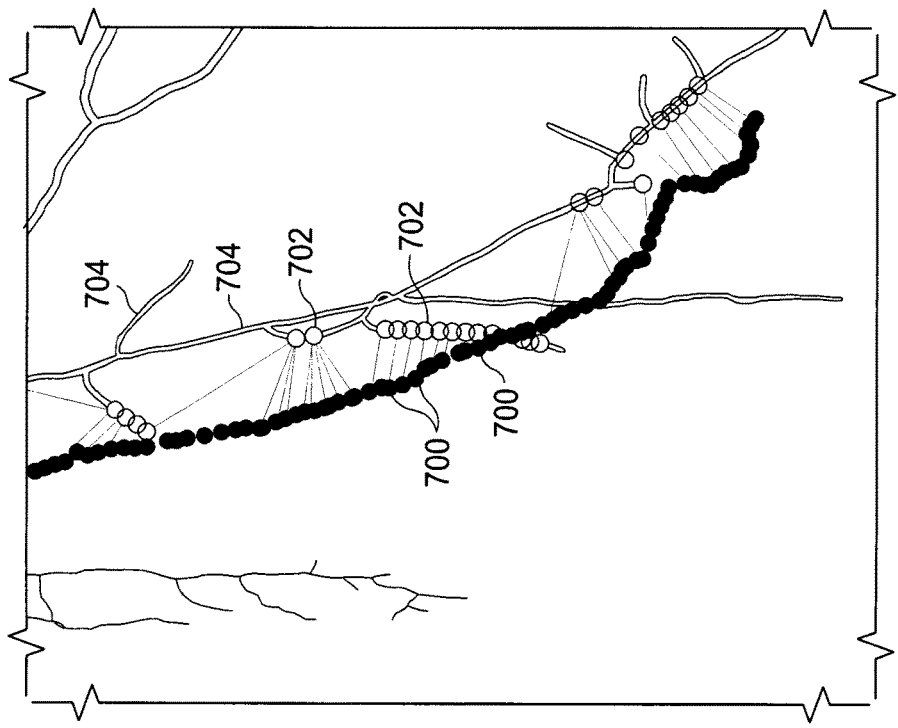

FIG. 7 illustrates temporally ordered sensor data 700 and candidate match points 702 along a series of centerline points 704 that correspond to anatomic passageways in an anatomic model. In this illustration, the temporally ordered sensor data 700 and the candidate points 702 are matched only based upon their individual position without pair-wise constraints, which generates error in that candidate points are located in discontinuous branches of the anatomic passageway tree. FIG. 8 illustrates a more optimized registration using the techniques described above. In this embodiment, the temporally ordered sensor data 800 is matched to candidate points 802 on contiguous branches of the anatomic passageway tree.

Figure 9:
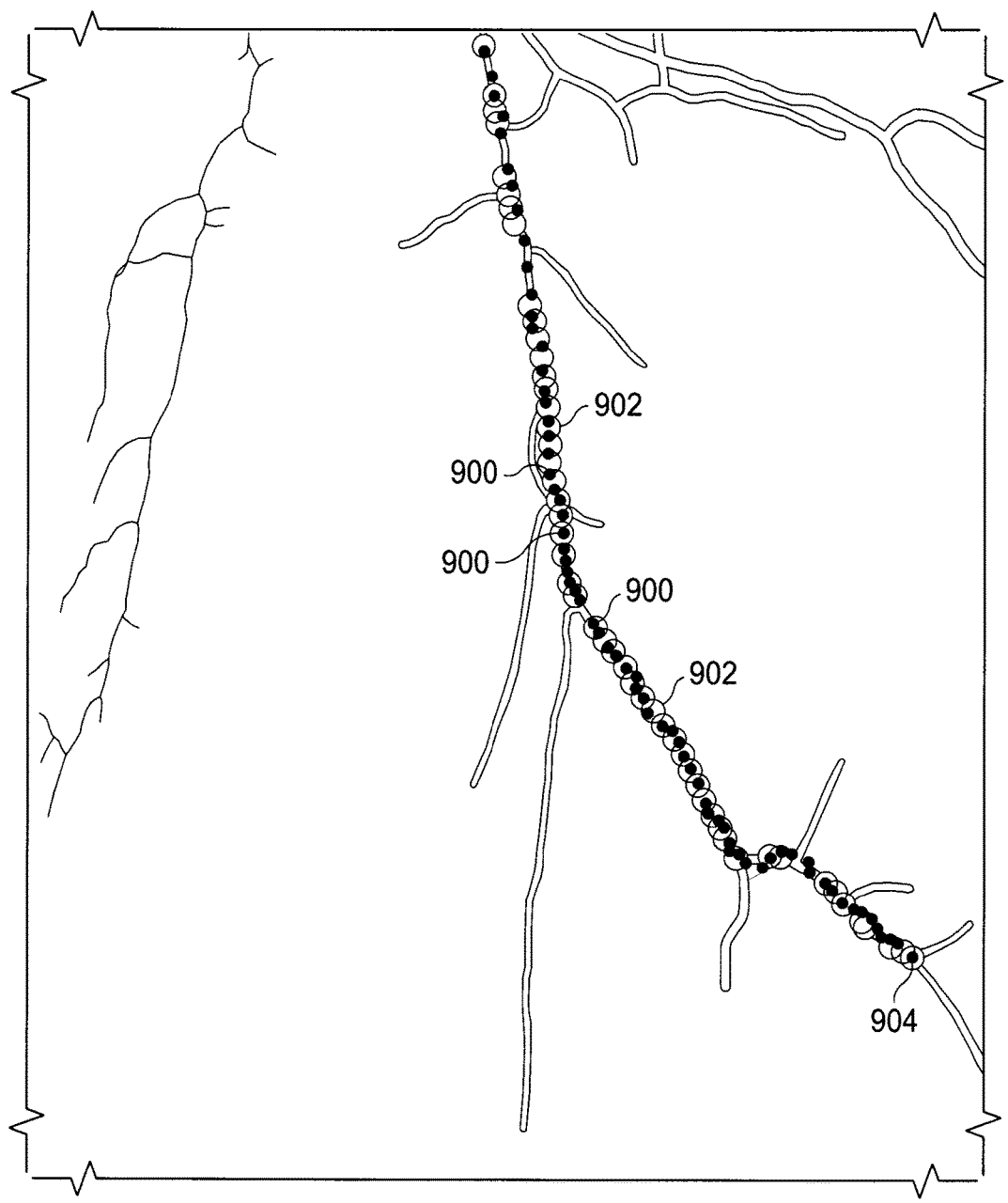
FIG. 9 illustrates temporally ordered sensor data registered to the model of anatomic passageways.
Figure 10:
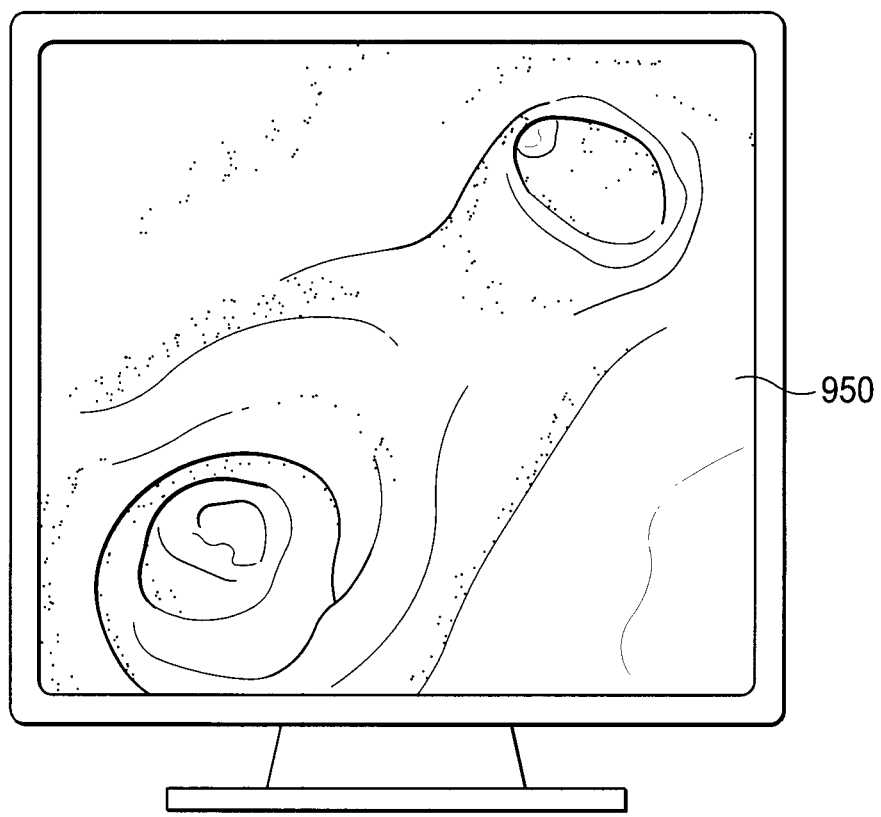
FIG. 10 illustrates a virtual image of the patient anatomy from the viewpoint of the registered interventional instrument.

FIG. 9 graphically illustrates the registration of the temporally ordered sensor data 900 and the candidate match points 902. The most current sensor data at point 904 indicates that the tip of the catheter is currently located just proximal of a bifurcation in the modeled passageways. As shown in FIG. 10, with the tip of the catheter registered to the model, a virtual view 950 of the anatomic passageway bifurcation from perspective of the tip of the catheter is generated for display to the clinician. There may be other options to generate a virtual view indicative of the tip pose with respect to the model. As the catheter is advanced through the anatomic passageways, the processes described above are rapidly repeated to provide the clinician with a virtual view of the anatomic passageways that corresponds to the current pose of the tip of the catheter. The virtual views allow the clinician to guide the catheter through the passageways without reliance on real cameras. For example, when the passageways become too small to accommodate a camera or when the camera view becomes obstructed by blood or mucous, the catheter can be guided by the virtual visualization system.

Although the registration systems and methods have been described herein with respect to tele-operated or hand operated interventional systems, these registration systems and methods will find application in a variety of medical and non-medical instruments in which accurate instrument image registration is required.

Although the systems and methods of this disclosure have been described for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-interventional applications.

One or more elements in embodiments of the invention may be implemented in software to execute on a processor of a computer system such as control system 116. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method of tracking a medical instrument in a formation of anatomical passageways, the method comprising:
   receiving, by a control system, a model of the anatomical passageways;
   identifying, by the control system, one or more centerlines of the modeled anatomical passageways, the centerlines including a set of candidate match points of the model, wherein each of the candidate match points includes three-dimensional coordinates in a model space;
   receiving, by the control system and while the medical instrument is positioned within the anatomical passageways, a set of ordered sensor records generated by one or more sensors of the medical instrument, the set providing a path history of the medical instrument in the anatomical passageways, wherein each sensor record of the set includes three-dimensional coordinates in a patient coordinate space;
   determining, by the control system, a relationship between a first sensor record of the set of ordered sensor records, a second sensor record of the set of ordered sensor records, a first candidate match point of the set of candidate match points, and a second candidate match point of the set of candidate match points, wherein the relationship includes a comparison of the three-dimensional coordinates of the first and second sensor records in the patient coordinate space with the three-dimensional coordinates of the first and second candidate match points in the model space;
   registering, by the control system, the medical instrument with the model of the anatomical passageways based on the path history and the relationship to locate the medical instrument within the model of the anatomical passageways;
   displaying a virtual visualization image in a display system, the virtual visualization image being based on the registering of the medical instrument with the model of the anatomical passageway and depicting a rendered view of the model of the anatomical passageways from a perspective of the medical instrument within the model of the anatomical passageways; and
   implementing, by the control system, commands to move the medical instrument based on the registering of the medical instrument with the model of the anatomical passageway.

2. The method of claim 1 wherein the one or more sensors of the medical instrument include an electromagnetic sensor system having an electromagnetic sensor and shape sensor system having an optical fiber and the set of ordered sensor records include position information expressed as three-dimensional coordinates, orientation information, and shape information.

3. The method of claim 1 wherein determining the relationship includes determining a transition probability indicative of a likelihood that the first and second candidate match points are a best match to the first and second sensor records, wherein the first and second candidate match points are sequential candidate match points and the first and second sensor records are sequential sensor records.

4. The method of claim 1 further comprising tracking the movement of the medical instrument relative to the model of the anatomical passageways.

5. The method of claim 1 wherein the set of ordered sensor records include a set of temporally ordered sensor records.

6. The method of claim 1 wherein the set of ordered sensor records include a set of spatially ordered sensor records corresponding to more than one branch in the anatomical passageways.

7. The method of claim 1 wherein receiving the model of the anatomical passageways includes receiving the model formed from a set of three-dimensional volumetric images.

8. The method of claim 1 wherein receiving a set of ordered sensor records includes receiving the set from an electromagnetic sensor coupled to the medical instrument.

9. The method of claim 1 wherein the set of ordered sensor records includes temporally ordered pose observations for a tip of the medical instrument.

10. The method of claim 1 wherein the set of ordered sensor records includes temporally ordered shape observations for a portion of the medical instrument.

11. The method of claim 1 further comprising filtering the received set of ordered sensor records.

12. The method of claim 11 wherein filtering the received set of ordered sensor records includes creating a subset of the ordered sensor records that includes only sensor data recorded at a selected phase of anatomical movement.

13. The method of claim 12 wherein the selected phase of anatomical movement is an expiration phase of a breathing cycle of a lung.

14. The method of claim 3 wherein determining the transition probability includes determining a distance between the first and second candidate match points.

15. The method of claim 3 wherein determining the transition probability includes determining a distance between a first sensor record associated with the first candidate match point and a second sensor record associated with the second candidate match point.

16. The method of claim 3 wherein determining the transition probability includes determining whether the first and second candidate match points are in contiguous passageways of the model of the anatomical passageways.

17. A method of tracking a medical instrument in a formation of anatomical passageways, the method comprising:
   receiving, by a control system, a model of the anatomical passageways;
   identifying, by the control system, one or more centerlines of the modeled anatomical passageways, the centerlines including a set of candidate match points of the model, wherein each of the candidate match points includes three-dimensional coordinates in a model space;
   receiving, by the control system, a set of ordered sensor records generated by one or more sensors of the medical instrument while disposed in the anatomical passageways, the set providing a path history of the medical instrument in the anatomical passageways, wherein each sensor record of the set includes three-dimensional coordinates in a patient coordinate space;
   spatially subsampling the set of ordered sensor records such that no more than one sensor record per unit of spatial resolution is included in a subsampled set of ordered sensor records, the unit of spatial resolution corresponding to a spatial resolution of an imaging technology used in generating the model of the anatomical passageways;

determining, by the control system, a relationship between a first sensor record of the subsampled set of ordered sensor records, a second sensor record of the subsampled set of ordered sensor records, a first candidate match point of the set of candidate match points, and a second candidate match point of the set of candidate match points, wherein the relationship includes a comparison of the three-dimensional coordinates of the first and second sensor records in the patient coordinate space with the three-dimensional coordinates of the first and second candidate match points in the model space;

registering, by the control system, the medical instrument with the model of the anatomical passageways based on the path history and the relationship;

displaying a virtual visualization image in a display system, the virtual visualization image being based on the registering of the medical instrument with the model of the anatomical passageway and depicting a view of the model of the anatomical passageways from a perspective of the medical instrument; and implementing, by the control system, commands to move the medical instrument based on the registering of the medical instrument with the model of the anatomical passageways.

18. The method of claim 1 wherein registering includes comparing position data from at least one of the sensor records in the set of ordered sensor records to at least one of the candidate match points defined within a passageway in the model of the anatomical passageways.

19. The method of claim 1 wherein registering includes comparing orientation vector data from at least one of the sensor records in the set of ordered sensor records to at least one of the candidate match points defined within a passageway in the model of the anatomical passageways.

20. The method of claim 1 wherein displaying the virtual visualization image in the display system comprises displaying an internal virtual view of the anatomical passageways as the virtual visualization image.

21. A system for tracking a medical instrument in a formation of anatomical passageways, the system comprising:

a control system including a processor-readable storage medium and a processor configured to execute programmed instructions stored on the storage medium to:

receive a model of the anatomical passageways;

identify one or more centerlines of the modeled anatomical passageways, the centerlines including a set of candidate match points of the model, wherein each of the candidate match points includes three-dimensional coordinates in a model space;

receive a set of ordered sensor records generated by a sensor system of the medical instrument while the medical instrument is positioned within the anatomical passageways, the set of ordered sensor records providing a path history of the medical instrument in the anatomical passageways, wherein each sensor record of the set includes ordered position and orientation information from the sensor system, the position information including three-dimensional coordinates in a patient coordinate space;

determine a relationship between a first sensor record of the set of ordered sensor records, a second sensor record of the set of ordered sensor records, a first candidate match point of the set of candidate match points, and a second candidate match point of the set of candidate match points, wherein the relationship includes a comparison of the three-dimensional coordinates of the first and second sensor records in the patient coordinate space with the three-dimensional coordinates of the first and second candidate match points in the model space; and register the medical instrument with the model of the anatomical passageways based on the path history and the relationship to locate the medical instrument within the model of the anatomical passageways;

display a virtual visualization image in a display system, the virtual visualization image being based on registering of the medical instrument with the model of the anatomical passageway and depicting a view of the model of the anatomical passageways from a perspective of the medical instrument; and implement, by the control system, commands to move the medical instrument based on the registering of the medical instrument with the model of the anatomical passageways.

22. The system of claim 21 further comprising the medical instrument equipped with the sensor system.

23. The system of claim 21 wherein the medical instrument includes an elongated flexible body.

24. The system of claim 21 wherein the sensor system includes an electromagnetic sensor.

25. The system of claim 24 wherein the sensor system further includes a fiber optic shape sensor.

26. The system of claim 21 wherein determining the relationship includes determining a transition probability indicative of a likelihood that the first and second candidate match points are a best match to the first and second sensor records, wherein the first and second candidate match points are sequential candidate match points and the first and second sensor records are sequential sensor records.

27. The system of claim 21 wherein the processor is further configured for tracking the movement of the medical instrument relative to the model of the anatomical passageways.

28. The system of claim 21 wherein the set of ordered sensor records include a set of temporally ordered sensor records.

29. The system of claim 21 wherein the set of ordered sensor records include a set of spatially ordered sensor records.

30. The system of claim 21 wherein receiving the model of the anatomical passageways includes receiving the model formed from a set of three-dimensional volumetric images.

31. The system of claim 21 wherein receiving a set of ordered sensor records includes receiving the set from an electromagnetic sensor coupled to the medical instrument.

32. The system of claim 21 wherein the set of ordered sensor records includes temporally ordered pose observations for a tip of the medical instrument.

33. The system of claim 21 wherein the set of ordered sensor records includes temporally ordered shape observations for a portion of the medical instrument.

34. The system of claim 21 wherein registering includes filtering the received set of ordered sensor records.

35. The system of claim 34 wherein filtering the received set of ordered sensor records includes creating a subset of the ordered sensor records that includes only sensor data recorded at a selected phase of anatomical movement.

36. The system of claim 35 wherein the selected phase of anatomical movement is an expiration phase of a breathing cycle of a lung.

37. The system of claim 26 wherein determining the transition probability includes determining a distance between the first and second candidate match points.

38. The system of claim 26 wherein determining the transition probability includes determining a distance between a first sensor record associated with the first candidate match point and a second sensor record associated with the second candidate match point.

39. The system of claim 26 wherein determining the transition probability includes determining whether the first and second candidate match points are in contiguous passageways of the model of the anatomical passageways.

40. The system of claim 21 wherein the processor is further configured for spatially subsampling the set of ordered sensor records such that no more than one sensor record per unit of spatial resolution is included in a sub-sampled set of ordered sensor records.

41. The system of claim 21 wherein registering includes comparing position data from at least one of the sensor records in the set of ordered sensor records to at least one of the candidate match points defined within a passageway in the model of the anatomical passageways.

42. The system of claim 21 wherein registering includes comparing orientation vector data from at least one of the sensor records in the set of ordered sensor records to at least one of the candidate match points defined within a passageway in the model of the anatomical passageways.

43. The system of claim 21 further comprising a display for displaying an internal virtual view of the anatomical passageways.

* * * * *